US011452856B2

(12) United States Patent
Kakinoki

(10) Patent No.: US 11,452,856 B2
(45) Date of Patent: Sep. 27, 2022

(54) MEDICAL DEVICE

(71) Applicant: TERUMO KABUSHIKI KAISHA, Tokyo (JP)

(72) Inventor: Toshihiko Kakinoki, Oyama (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 357 days.

(21) Appl. No.: 16/560,058

(22) Filed: Sep. 4, 2019

(65) Prior Publication Data

US 2019/0388673 A1    Dec. 26, 2019

Related U.S. Application Data

(63) Continuation of application No. PCT/JP2018/011486, filed on Mar. 22, 2018.

(30) Foreign Application Priority Data

Mar. 24, 2017    (JP) .............................. JP2017-058828

(51) Int. Cl.
    *A61M 39/26*    (2006.01)
    *A61M 39/10*    (2006.01)
    *A61M 5/14*     (2006.01)

(52) U.S. Cl.
    CPC ........ *A61M 39/1011* (2013.01); *A61M 39/26* (2013.01); *A61M 5/14* (2013.01)

(58) Field of Classification Search
    CPC .............. A61M 39/1011; A61M 39/26; A61M 2039/1033
    See application file for complete search history.

(56) References Cited

U.S. PATENT DOCUMENTS

| 8,157,784 B2 | 4/2012 | Rogers |
| 2003/0032940 A1* | 2/2003 | Doyle .................. A61M 39/26 604/533 |
| 2012/0157914 A1* | 6/2012 | Stroup .................. A61M 39/10 604/207 |

(Continued)

FOREIGN PATENT DOCUMENTS

| JP | S51-40971 Y2 | 10/1976 |
| JP | 2002526179 A | 8/2002 |

(Continued)

OTHER PUBLICATIONS

International Search Report (PCT/ISA/210) dated Jun. 12, 2018, by the Japan Patent Office as the International Searching Authority for International Application No. PCT/JP2018/011486.

(Continued)

*Primary Examiner* — Nathan R Price
*Assistant Examiner* — Courtney B Fredrickson
(74) *Attorney, Agent, or Firm* — Buchanan Ingersoll & Rooney PC

(57) ABSTRACT

A medical device including a connector portion having a distal end and a proximal end, and a screw groove configured for fluid communication between the connector portion and another medical device. The screw groove has a first side wall provided close to the distal end and a second side wall provided close to the proximal end. The first side wall has a stop portion whose lead angle has been reduced or eliminated.

14 Claims, 10 Drawing Sheets

(56) References Cited

U.S. PATENT DOCUMENTS

| | | | | |
|---|---|---|---|---|
| 2014/0276458 A1* | 9/2014 | Mansour | ............... | A61M 39/22 |
| | | | | 604/256 |
| 2014/0303601 A1* | 10/2014 | Fangrow | ............... | A61M 39/10 |
| | | | | 604/537 |
| 2016/0045629 A1* | 2/2016 | Gardner | .................... | A61L 2/18 |
| | | | | 422/292 |

FOREIGN PATENT DOCUMENTS

| | | |
|---|---|---|
| JP | 2003106321 A | 4/2003 |
| JP | 2011020730 A | 2/2011 |
| WO | 2016051759 A1 | 4/2016 |

OTHER PUBLICATIONS

An English Translation of the International Search Report (Form PCT/ISA/210) and the Written Opinion of the International Searching Authority (Form PCT/ISA/237) dated Jun. 12, 2018, by the Japanese Patent Office in corresponding International Application No. PCT/JP2018/011486. (7 pages).

* cited by examiner

MEDICAL DEVICE

CROSS-REFERENCES TO RELATED APPLICATIONS

This application is a continuation of International Application No. PCT/JP2018/011486 filed on Mar. 22, 2018, which claims priority to Japanese Application No. 2017-058828 filed on Mar. 24, 2017, the entire content of both of which is incorporated herein by reference.

TECHNICAL FIELD

The present disclosure relates to a medical device.

DESCRIPTION

Conventionally, among medical devices used for infusion into a living body such as a human body, a medical connector or a syringe having a connector portion are known. Such a medical device sometimes includes a screw groove configured for fluid communication between the connector portion and another medical device.

For example, U.S. Pat. No. 8,157,784 discloses a medical connector (medical device) including a closed male connector portion that can be closed by a valve body, the medical connector further including a screw groove configured for fluid communication between the male connector portion and a female connector portion of another medical connector (another medical device). The female connector portion of another medical connector is a closed female connector portion that can be closed by an elastic valve. Further, another medical connector is screwed along the screw groove so that a spike provided on the male connector portion penetrates the valve body and the elastic valve in contact with each other, whereby the male connector portion and the female connector portion can be connected in such a manner that a fluid communicates between the male connector portion and the female connector portion.

In the medical device (medical connector) as described in U.S. Pat. No. 8,157,784, there is a risk that a screw is loosened and the fluid communication is released unintentionally depending on setting of a lead angle of the screw groove in a fluid communication state between the connector portion (closed male connector portion) and another medical device (another medical connector) when an external force in a direction (separation direction) to separate the medical devices from each other is applied, that is, when an external force in a pulling direction is applied.

In addition, the medical device described in U.S. Pat. No. 8,157,784 is configured such that the valve body biases another medical device in the separation direction and the valve body is pressed against the elastic valve when another medical device is screwed along the screw groove. In this manner, the screw can be easily loosened when the external force in the pulling direction is applied particularly in the case where the valve body is configured to bias another medical device in the separation direction.

SUMMARY

A medical device is disclosed, which includes a connector portion capable of suppressing an unintentional release of fluid communication due to an application of an external force in a pulling direction.

A medical device as a first aspect of the present disclosure is a medical device including: a connector portion having a distal end and a proximal end, and a screw groove configured for fluid communication between the connector portion and another medical device, in which the screw groove has a first side wall on a distal side of the screw groove and a second side wall on a proximal side of the screw groove, and the first side wall has a stop portion whose lead angle has been reduced or eliminated.

In accordance with an embodiment of the present disclosure, the connector portion has an outer cylinder and an inner cylinder arranged on a radially inner side of the outer cylinder, and the outer cylinder has the screw groove, and the inner cylinder has an engagement protrusion which is guided to the screw groove.

In accordance with an embodiment of the present disclosure, the inner cylinder is biased toward the distal end.

In accordance with an embodiment of the present disclosure, the engagement protrusion is in point contact with the stop portion.

In accordance with an embodiment of the present disclosure, the medical device further includes a stopper that abuts on the engagement protrusion, which has reached the stop portion, so as to prevent the engagement protrusion from moving toward the proximal end.

In accordance with an embodiment of the present disclosure, the connector portion further has a valve body arranged on a radially inner side of the inner cylinder, and a spike capable of penetrating the valve body.

A medical device as a second aspect of the present disclosure is a medical device including a connector portion having a distal end and a proximal end, in which the connector portion has an outer cylinder and an inner cylinder arranged on a radially inner side of the outer cylinder, the inner cylinder has a screw groove configured for fluid communication between the connector portion and another medical device, and the outer cylinder has an engagement protrusion guided to the screw groove, the screw groove has a first side wall on the distal side of the screw groove and a second side wall on the proximal side of the screw groove, and the second side wall has a stop portion whose lead angle has been reduced or eliminated.

A medical device as a third aspect of the present disclosure is a medical device including: a connector portion having a distal end, a proximal end and a central axis; and a screw groove for fluid communication between the connector portion and another medical device, in which the screw groove has a first side wall on the distal side of the screw groove, a second side wall on the proximal side of the screw groove, and a bottom wall interconnecting the first side wall and the second side wall, and the bottom wall has a widening portion whose width in a direction along the central axis increases.

According to the present disclosure, it is possible to provide the medical device including the connector portion capable of suppressing the unintentional release of fluid communication due to the application of the external force in the pulling direction.

DESCRIPTION OF EMBODIMENTS

Figure 1:
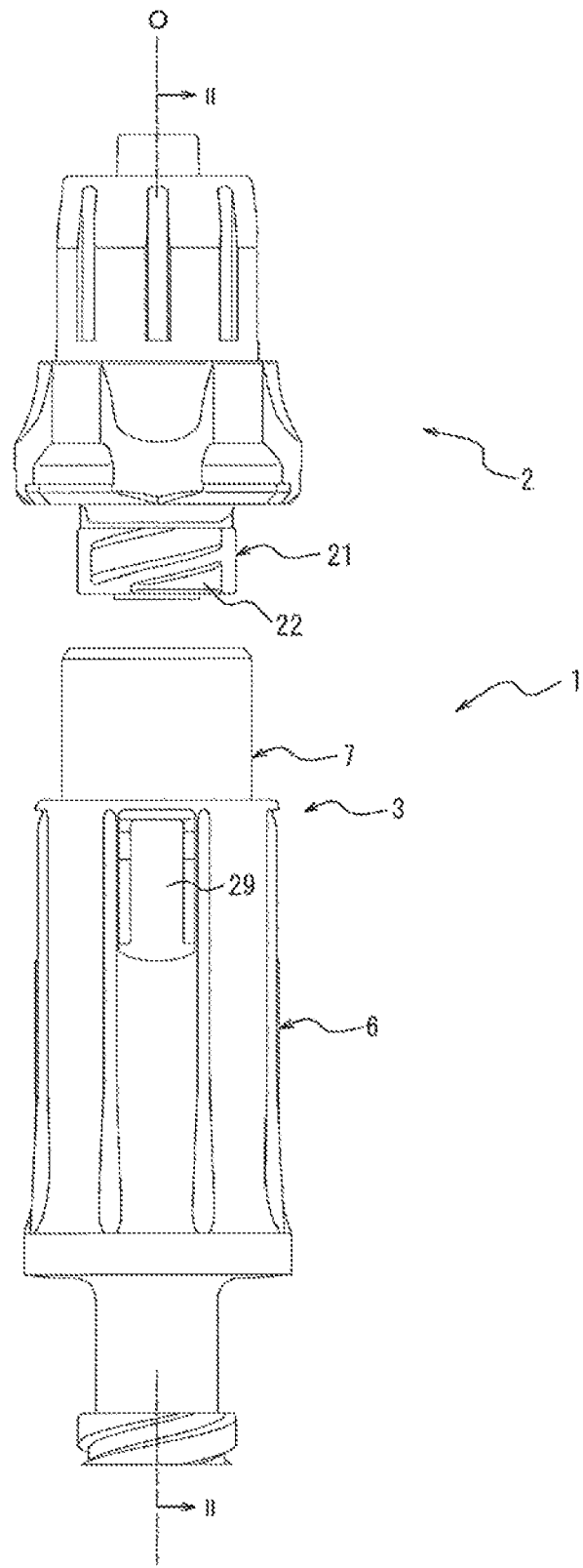
FIG. 1 is a side view illustrating a medical device according to a first embodiment of the present disclosure together with another medical device.

Hereinafter, a medical device according to one embodiment of the present disclosure will be illustrated and described in detail with reference to the drawings. First, a medical device 1 according to a first embodiment of the present disclosure will be illustrated and described in detail with reference to FIGS. 1 to 7B. As illustrated in FIG. 1, the medical device 1 according to the present embodiment is configured as a medical connector used for infusion into a living body such as a human body, and includes a connector portion 3 capable of fluid communication with another medical device (in this example, a medical connector) 2. The medical device 1 may be configured as a syringe or the like which is used for infusion into a living body such as a human body.

Figure 2:
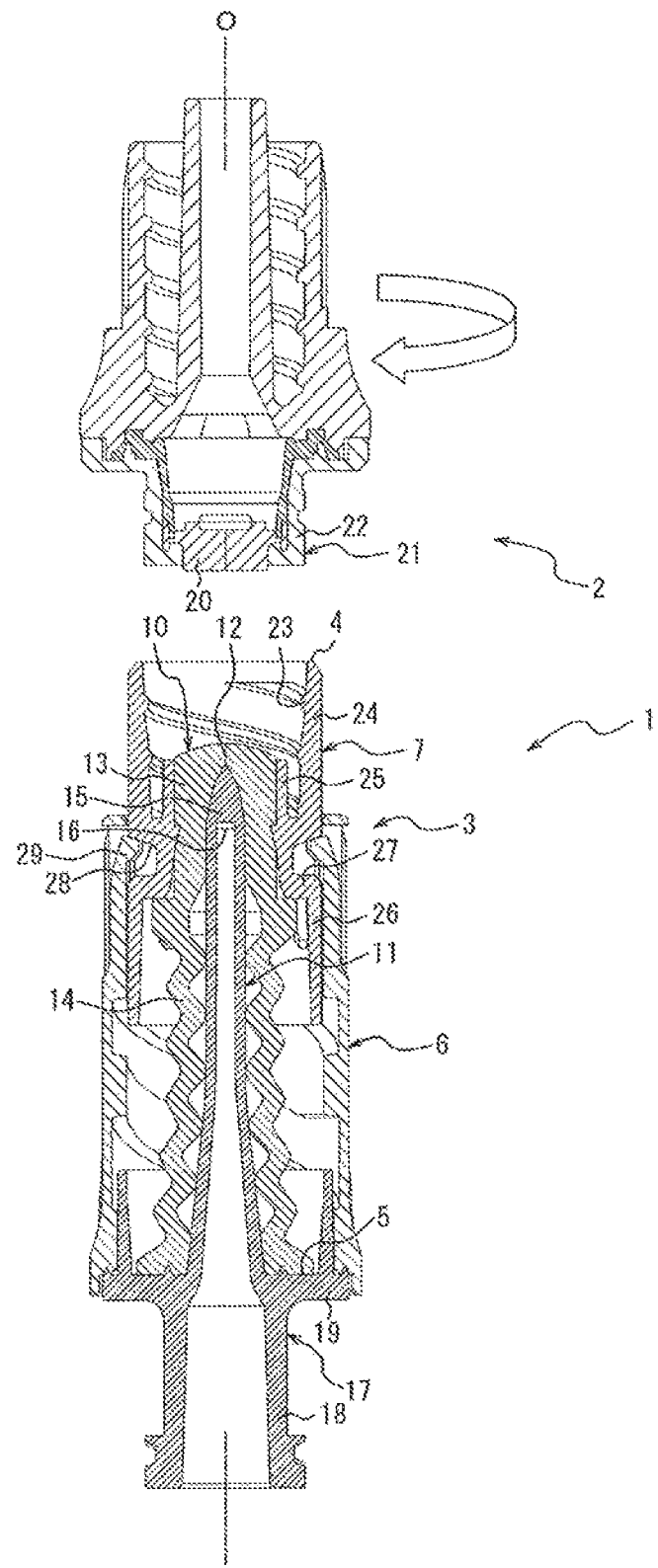
FIG. 2 is a cross-sectional view taken along line II-II of FIG. 1.
Figure 3:
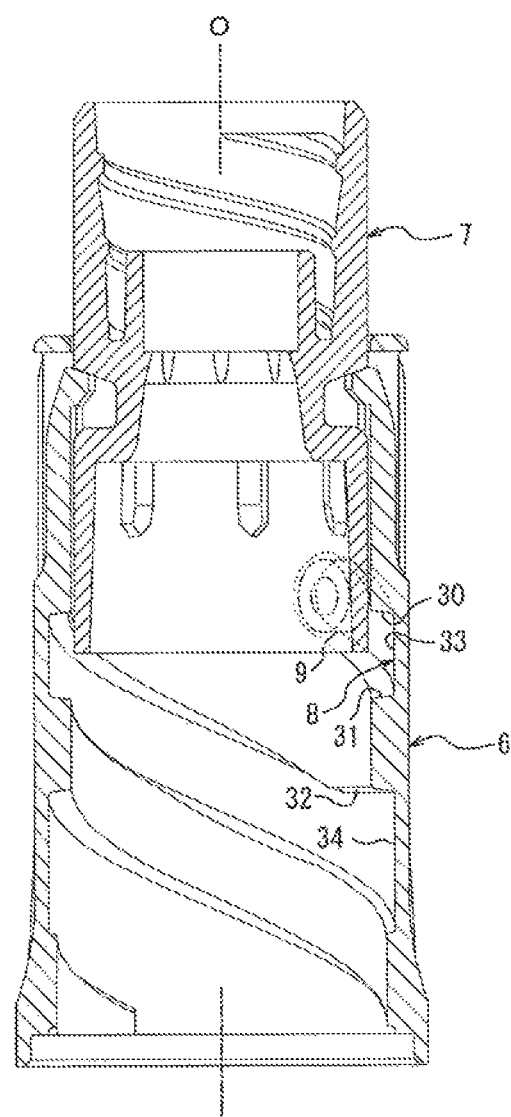
FIG. 3 is a cross-sectional view illustrating only an inner cylinder and an outer cylinder in the medical device according to the first embodiment with reference to FIG. 2.

As illustrated in FIG. 2, the connector portion 3 has a distal end 4, a proximal end 5, and a central axis O. In addition, the connector portion 3 has an outer cylinder 6 and an inner cylinder 7 arranged on a radially inner side of the outer cylinder 6 in the present embodiment. Further, the outer cylinder 6 has a screw groove 8 configured for fluid communication between the connector portion 3 and another medical device 2, and the inner cylinder 7 has an engagement protrusion 9 which is guided to the screw groove 8 in the present embodiment as illustrated in FIG. 3. In the present embodiment, the screw groove 8 is configured as a double thread groove, and the engagement protrusion 9 is configured as two protrusions corresponding to the double thread groove. However, the screw groove 8 may be a single thread groove or triple or more thread groove. In addition, the engagement protrusion 9 is configured as a cylindrical protrusion in the present embodiment, but a shape of the engagement protrusion 9 is not particularly limited as long as the engagement protrusion 9 has a protrusion which is guided to the screw groove 8.

In accordance with the present embodiment, the connector portion 3 includes a valve body 10 arranged on a radially inner side of the inner cylinder 7 and a spike 11 capable of penetrating the valve body 10 as illustrated in FIG. 2. The valve body 10 has an apical cylindrical head portion 13 having a slit 12 through which the spike 11 can penetrate, and a body portion 14 which can be elastically deformed in a direction along the central axis O (hereinafter also referred to as an axial direction). In accordance with an exemplary embodiment, the body portion 14 is stretchable by being formed in a bellows shape. In accordance with an exemplary embodiment, the head portion 13 and the body portion 14 of the valve body 10 are integrally formed, but may be separately formed. In addition, for example, a coil spring may be used instead of the body portion 14.

In accordance with an exemplary embodiment, the spike 11 has a cylindrical shape which extends in the axial direction and which is closed by the distal end portion 15, and the distal end portion 15 is formed in a sharp pointed shape. In addition, a communicating hole 16 penetrating the spike 11 is formed on a side surface of the distal end portion 15. Therefore, when the spike 11 penetrates the head portion 13 of the valve body 10, the spike 11 can form a flow path of a fluid such as a chemical solution inside the spike 11 (see FIG. 5 described later). In the present embodiment, the spike 11 constitutes a part of a flow path formation member 17. The flow path formation member 17 has a female connector portion 18 connected to a proximal end portion of the spike 11 and a flange 19 connected to a proximal end portion of the outer cylinder 6.

Figure 4:
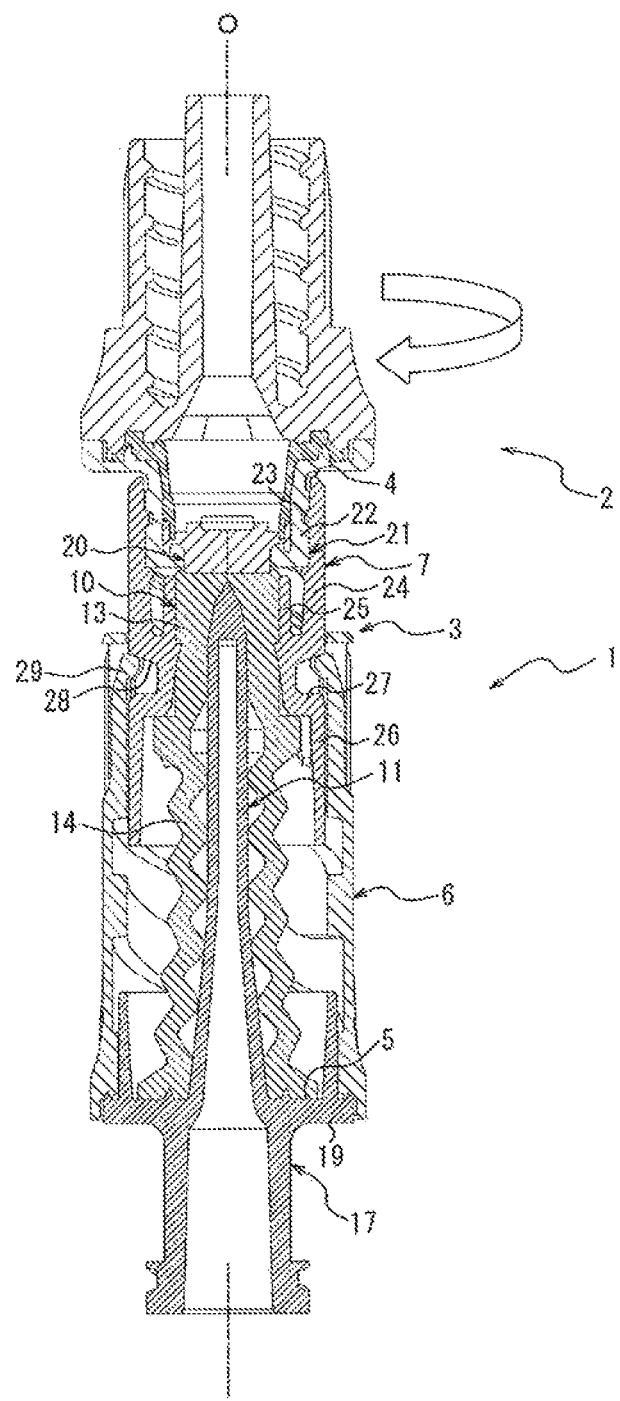
FIG. 4 is a cross-sectional view illustrating a state where another medical device is connected to the inner cylinder of the medical device according to the first embodiment with reference to FIG. 2.

Another medical device 2 has a closed female connector portion 21 which can be closed by an elastic valve 20. Further, the connector portion 3 of the medical device 1 is configured to move the inner cylinder 7 in the axial direction with respect to the outer cylinder 6 in a state where another medical device 2 is connected to the inner cylinder 7 so that the valve body 10 is pressed against the elastic valve 20 as illustrated in FIG. 4, thereby switching presence or absence of fluid communication between the connector portion 3 and another medical device 2. That is, the connector portion 3 and another medical device 2 are not connected in such a manner that a fluid communicates between the connector portion 3 and the another medical device 2 in the state illustrated in FIG. 4, but the connector portion 3 and another medical device 2 are connected in such a manner that a fluid communicates between the connector portion 3 and the another medical device 2 in a state illustrated in FIG. 5.

In accordance with an exemplary embodiment, the inner cylinder 7 has a tubular connection cylinder 24 having on a screw portion 23, which is engaged with a screw portion 22 provided on an outer circumferential surface of the female connector portion 21 of another medical device 2, on an inner circumferential surface. In addition, the inner cylinder 7 has a cylindrical enclosure cylinder 25 which is connected to a proximal end portion of the connection cylinder 24 and encloses the head portion 13 of the valve body 10. A lower end portion of the enclosure cylinder 25 is connected to a distal end portion of a tubular engagement cylinder 26 having the engagement protrusion 9 (see FIG. 5) on an outer circumferential surface. An annular step portion 27 extending in a radial direction is formed at a connecting portion between the enclosure cylinder 25 and the engagement cylinder 26. A distal end portion of the body portion 14 of the valve body 10 abuts on the annular step portion 27, and a proximal end portion of the body portion 14 abuts on the flange 19 of the flow path formation member 17. In this manner, the inner cylinder 7 is biased (i.e., located) toward the distal end 4 by the body portion 14 of the valve body 10 in the present embodiment.

In addition, a locking recess 28 (in this example, formed in an annular shape) is provided between the connection cylinder 24 and the engagement cylinder 26 as a locking portion that can be locked to the outer cylinder 6, and the outer cylinder 6 is provided with locking claws 29 (in this example, four locking claws are arranged at equal intervals in a circumferential direction) that can be locked to the locking recess 28.

Figure 5:
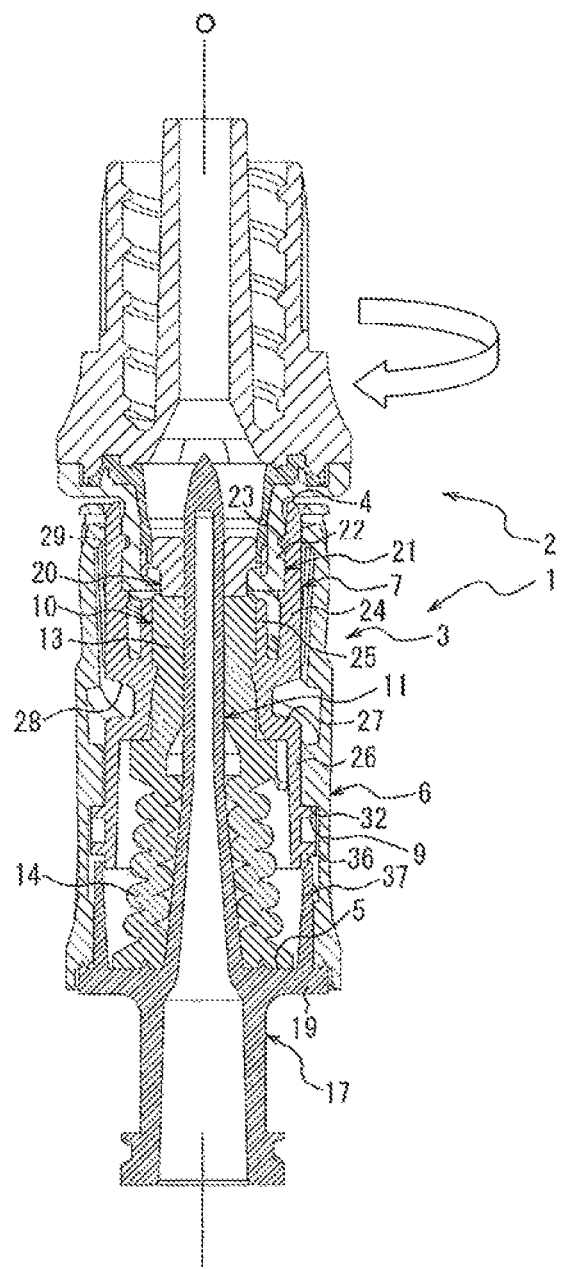
FIG. 5 is a cross-sectional view illustrating a state where another medical device is connected to the medical device according to the first embodiment in such a manner that a fluid communicates between the another medical device and the medical device with reference to FIG. 2.

Further, when another medical device 2 is screwed into the inner cylinder 7 as illustrated in FIG. 4 in a state where the inner cylinder 7 is locked to the outer cylinder 6, the valve body 10 is pressed against the elastic valve 20, and another medical device 2 is connected to the inner cylinder 7. Then, when another medical device 2 is rotated in the same direction as when screwed into the inner cylinder 7, the engagement between the outer cylinder 6 and the inner cylinder 7 is released as the locking claws 29 are separated from the locking recess 28, the engagement protrusion 9 of the inner cylinder 7 is guided toward the proximal end 5 along the screw groove 8 of the outer cylinder 6, the head portion 13 of the valve body 10 and the elastic valve 20 move toward the proximal end 5 together with the inner cylinder 7, the head portion 13 and the elastic valve 20 are penetrated by the spike 11, and the connector portion 3 and another medical device 2 are connected in such a manner that a fluid communicates between the connector portion 3 and the another medical device 2 as illustrated in FIG. 5. Another medical device 2 may be rotated in the opposite direction to the above direction with respect to the medical device 1 in order to separate the medical device 1 and another medical device 2 from each other.

Figure 6A:
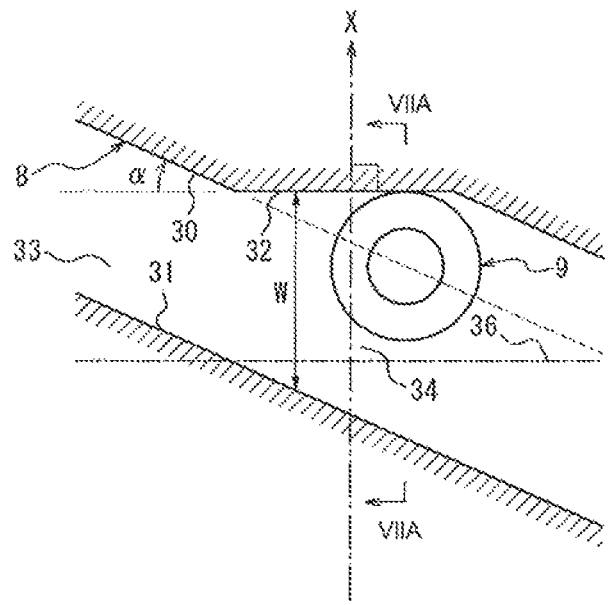
FIG. 6A is a developed view for describing an engagement state of a screw groove and an engagement protrusion in the state illustrated in FIG. 5.

In the present embodiment, the screw groove 8 has a first side wall 30 on a distal side of the screw groove 8 (i.e., provided close to the distal end 4) and a second side wall 31 on a proximal side of the screw groove 8 (i.e., provided close to the proximal end 5) as illustrated in FIGS. 3 and 6A. In FIG. 6A, an arrow X indicates an axially distal end side (the distal end 4 side in the direction along the central axis O). Further, the first side wall 30 has a stop portion 32 having a lead angle α of zero (i.e., in a direction orthogonal to the central axis O) at a terminal end on the proximal end 5 side of the screw groove 8 (a terminal end of a movable range of the engagement protrusion 9) in the present embodiment. Accordingly, the engagement protrusion 9 of the inner cylinder 7 is in contact with the stop portion 32 in a state where the connector portion 3 and another medical device 2 are connected in such a manner that a fluid communicates between the connector portion 3 and the another medical device 2 and screwing of the inner cylinder 7 to the outer cylinder 6 has been completed as illustrated in FIG. 5. Thus, even if an external force in a direction (separation direction) to separate the medical device 1 and another medical device 2, that is, an external force in a pulling direction is applied between the medical device 1 and another medical device 2, the engagement protrusion 9 of the inner cylinder 7 is supported by the stop portion 32 having the lead angle α of zero, and thus, the engagement protrusion 9 is not guided along the screw groove 8 toward the distal end 4 due to the external force in the pulling direction. Therefore, the inner cylinder 7 does not move toward the distal end 4 with respect to the outer cylinder 6 and the fluid communication is not released. In this manner, it is possible to suppress an unintentional release of fluid communication due to the application of the external force in the pulling direction according to the medical device 1 of the present embodiment.

According to the medical device 1 of the present embodiment, the inner cylinder 7 can be biased toward the distal end 4 (that is, in the separation direction) in the fluid communication state, and thus, the engagement protrusion 9 rather hardly moves from the stop portion 32, and it is possible to suppress the unintentional release of the fluid communication.

Figure 6B:
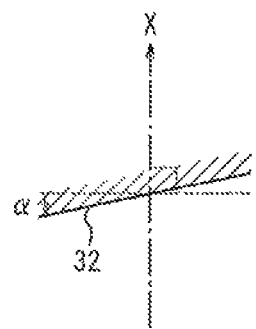
FIG. 6B is a modification of a stop portion illustrated in FIG. 6A.
Figure 6C:
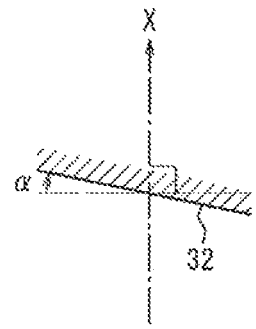
FIG. 6C is another modification of the stop portion illustrated in FIG. 6A.

In accordance with an exemplary embodiment, as long as the lead angle α of the stop portion 32 is a value close to zero even if being not zero, the same effect as the above effect can be obtained even in a case where the lead angle α of the stop portion 32 has a negative value, for example, as illustrated in FIG. 6B and a case where the lead angle α of the stop portion 32 has a positive value, for example, as illustrated in FIG. 6C. In addition, the stop portion 32 is not limited to a linear shape (planar shape) as illustrated in FIGS. 6A to 6C, and may have a curved shape (curved surface shape). In accordance with an exemplary embodiment, it can be sufficient for the stop portion 32 to be a portion where the lead angle α has been reduced (for example, smaller than the lead angle α in a portion other than the stop portion 32) or eliminated (for example, the lead angle α is zero or has a negative value), and the same effect as the above effect can be obtained with such a configuration.

In addition, the screw groove 8 has a bottom wall 33 interconnecting the first side wall 30 and the second side wall 31 in the present embodiment. Further, the bottom wall 33 has a widening portion 34 in which a width W of the axial direction increases. An end edge on the axially distal end side of the widening portion 34 is connected to the stop portion 32. In addition, the lead angle α of the second side wall 31 has the same size in a portion connected to the widening portion 34 and the other portion. Therefore, it is also possible to consider that the above-described effect that it is possible to suppress the unintentional release of fluid communication due to the application of the external force in the pulling direction can be obtained by providing the widening portion 34.

Figure 7A:
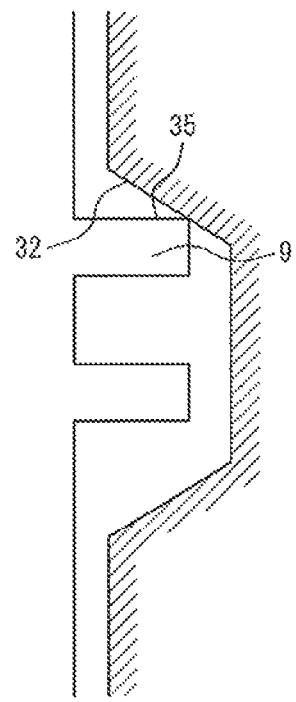
FIG. 7A is a cross-sectional view taken along line VIIA-VIIA of FIG. 6A.
Figure 7B:
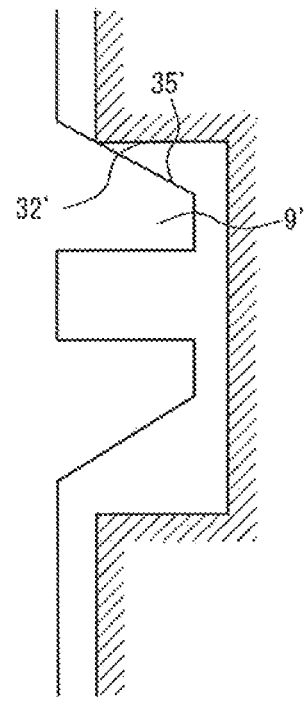
FIG. 7B is a modification of the screw groove and the engagement protrusion illustrated in FIG. 7A.

In accordance with an exemplary embodiment, the engagement protrusion 9 is configured to be in point contact (i.e., only a corner of the engagement protrusion 9 is in contact) with the stop portion 32 as illustrated in FIG. 7A in the present embodiment. That is, an inclination in a cross section of the outer circumferential surface 35 of the engagement protrusion 9 is different from an inclination in the cross section of the stop portion 32. The present disclosure is not limited to the shape as illustrated in FIG. 7A, but may have a shape illustrated in, for example, FIG. 7B, and the engagement protrusion 9 and the stop portion 32 may be in point contact with each other by another shape.

According to such a configuration, even when the engagement protrusion 9 is positioned at the stop portion 32, the fluid communication can be released by an operation of applying a relatively small torque. That is, the stop portion 32 is provided in the present embodiment, but a biasing force generated by the body portion 14 of the valve body 10 does not contribute to the reduction of the torque required to move the engagement protrusion 9 from the stop portion 32. Thus, when the engagement protrusion 9 is positioned at the stop portion 32, a torque that can be required for an operation of rotating the inner cylinder 7 with respect to the outer cylinder 6 increases as compared to a case where the engagement protrusion 9 is positioned in the other portion. If this torque is too large, another medical device 2 rotates with respect to the inner cylinder 7 before the inner cylinder 7 rotates with respect to the outer cylinder 6 when an operation of rotating another medical device 2 with respect to the medical device 1 has been performed to release the fluid communication, and as a result, there is a risk that a fluid leaks. In the present embodiment, however, the engagement protrusion 9 is configured to be in point contact with the stop portion 32 as described above, and thus, a frictional force between the engagement protrusion 9 and the stop portion 32 can be reduced, and the torque required to move the engagement protrusion 9 from the stop portion 32 can be reduced. Thus, the risk of the fluid leakage can be reduced.

In addition, the medical device 1 can include a stopper 36 that abuts on the engagement protrusion 9 having reached the stop portion 32 to help prevent the engagement protrusion 9 from moving toward the proximal end 5 as illustrated in FIGS. 5 and 6A in the present embodiment. Such a stopper 36 can help suppress rattling in the axial direction between the medical device 1 and another medical device 2 when a fluid communicates between the medical device 1 and the another medical device 2. In the present embodiment, the stopper 36 is configured using an upper end edge of the tubular-shaped cylindrical wall 37 provided on the flange 19 of the flow path formation member 17. Therefore, the outer cylinder 6 having the screw groove 8 in which the stop portion 32 has been formed can be rather easily formed by injection molding.

Although the stop portion 32 is provided at the terminal end of the screw groove 8 in the present embodiment, a position where the stop portion 32 is provided can be appropriately changed as long as a position can help suppress the unintentional release of fluid communication when the external force in the pulling direction is applied.

In addition, the outer cylinder 6, the inner cylinder 7, and the flow path formation member 17 can be formed by injection molding of a synthetic resin material, for example, but the material, a molding method, and the like are not particularly limited. In addition, the valve body 10 can be formed, for example, by injection molding of an elastic material such as rubber and a thermoplastic elastomer, but the material, a molding method, and the like are not particularly limited. Furthermore, each of the outer cylinder 6, the inner cylinder 7, the flow path formation member 17, and the valve body 10 is configured using one part in the present embodiment, but may be configured using a plurality of parts.

Figure 8:
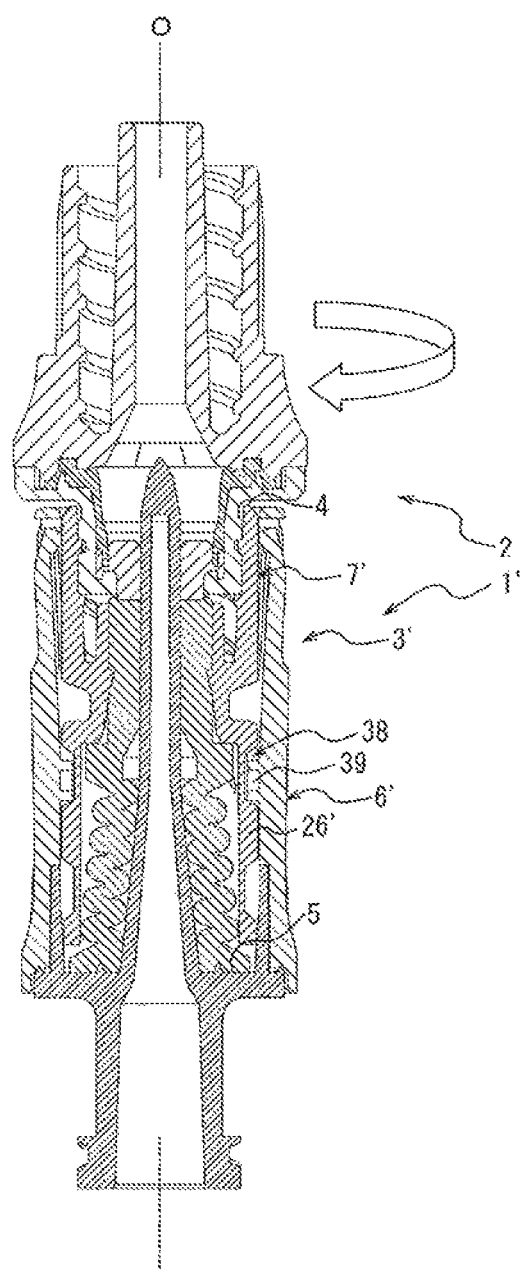
FIG. 8 is a cross-sectional view illustrating a state where another medical device is connected to a medical device according to a second embodiment of the present disclosure in such a manner that a fluid communicates between the another medical device and the medical device.
Figure 9:
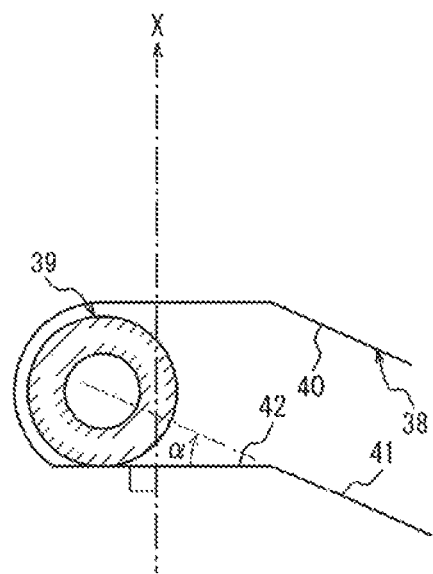
FIG. 9 is a developed view for describing an engagement state of a screw groove and an engagement protrusion in the state illustrated in FIG. 8.

Next, a medical device 1' according to a second embodiment of the present disclosure will be illustrated and described in detail with reference to FIGS. 8 and 9. The medical device 1' according to the present embodiment has the same configuration as that of the first embodiment except that positions of the screw groove 8 and the engagement protrusion 9 have been reversed. That is, a connector portion 3' includes an outer cylinder 6' and an inner cylinder 7' arranged on a radially inner side of the outer cylinder 6', the inner cylinder 7' has a screw groove 38 configured for fluid communication between the connector portion 3' and another medical device 2, and the outer cylinder 6' has an engagement protrusion 39 guided to the screw groove 38 as illustrated in FIG. 8 in the present embodiment. Further, the screw groove 38 has a first side wall 40 provided close to the distal end 4 and a second side wall 41 provided close to the proximal end 5, and the second side wall 41 has a stop portion 42 in which a lead angle α has been reduced or eliminated as illustrated in FIG. 9. The screw groove 38 can be provided in an engagement cylinder 26' of the outer cylinder 6', and an axial length, a diameter dimension and a thickness of the engagement cylinder 26' may be appropriately changed from those in the case of the first embodiment. Even with such a configuration, it is possible to suppress an unintentional release of fluid communication due to an application of an external force in a pulling direction, which is similar to the case of the first embodiment.

Figure 10A:
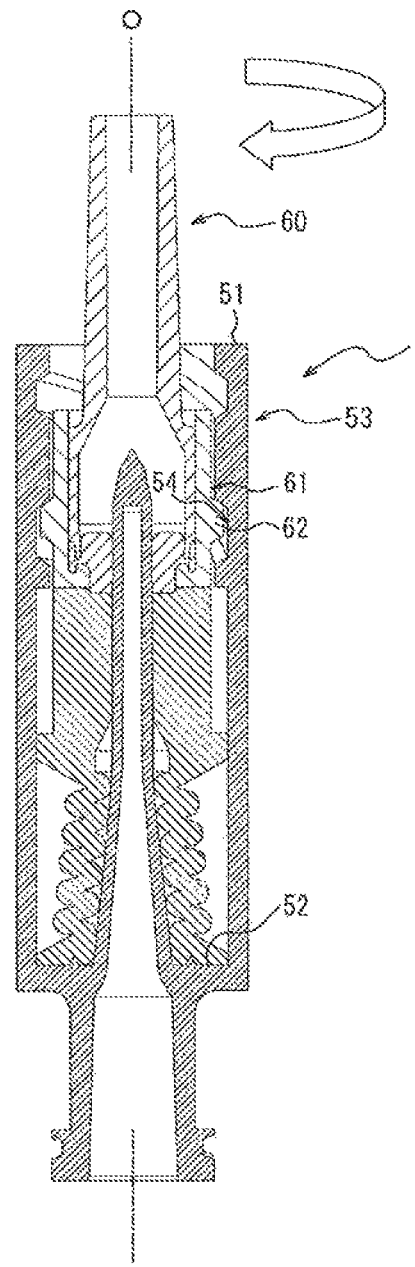
FIG. 10A is a cross-sectional view illustrating a state where another medical device is connected to a medical device according to a third embodiment of the present disclosure in such a manner that a fluid communicates between the another medical device and the medical device.
Figure 10B:
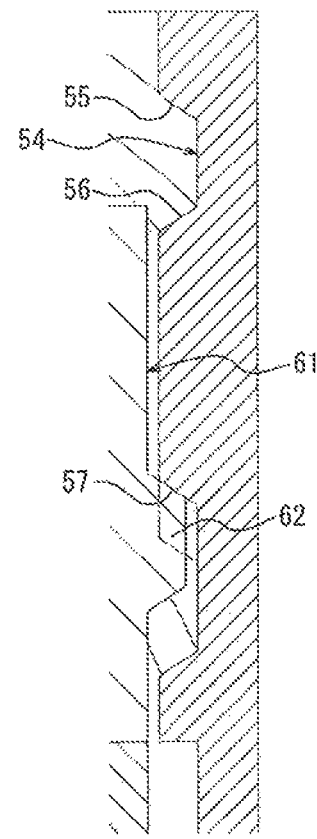
FIG. 10B is a partially enlarged view of FIG. 10A.

Next, a medical device 50 according to a third embodiment of the present disclosure will be illustrated and described in detail with reference to FIGS. 10A and 10B. The medical device 50 according to the present embodiment includes: a connector portion 53 having a distal end 51 and a proximal end 52; and a screw groove 54 for fluid communication between the connector portion 53 and another medical device 60. Further, the screw groove 54 has a first side wall 55 provided close to the distal end 51 and a second side wall 56 provided close to the proximal end 52, and the first side wall 55 has a stop portion 57 in which a lead angle α has been reduced or eliminated. In a fluid communication state illustrated in FIG. 10A, the engagement protrusion 62 provided on a female connector portion 61 of another medical device 60 is engaged with the stop portion 57. Even with such a configuration, it is possible to suppress an unintentional release of fluid communication due to an application of an external force in a pulling direction, which is similar to the case of the first embodiment.

Although one embodiment of the present disclosure has been described as above, the part described above only illustrate an example of embodiments of the present disclosure, and it is a matter of course that various changes may be applied within a scope not departing from a gist of the disclosure.

The detailed description above describes to a medical device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device comprising:
a connector portion having a distal end and a proximal end;
a screw groove configured for fluid communication between the connector portion and another medical device, wherein the screw groove has a first side wall on a distal side of the screw groove and a second side wall on a proximal side of the screw groove, and the first side wall has a stop portion whose lead angle changes slope relative to an adjacent first side wall portion;
the connector portion having an outer cylinder and an inner cylinder, the inner cylinder arranged on a radially inner side of the outer cylinder, the outer cylinder including the screw groove and the inner cylinder having an engagement protrusion which is guided to the screw groove;
the connector portion further includes a valve body arranged on a radially inner side of the inner cylinder, and a spike capable of penetrating the valve body; and
wherein the inner cylinder is biased toward the distal end by the valve body.

2. The medical device according to claim 1, wherein the engagement protrusion is in point contact with the stop portion.

3. The medical device according to claim 1, further comprising:
a stopper that abuts on the engagement protrusion, the engagement protrusion is configured to reach the stop portion, and wherein the stop portion is configured to prevent the engagement protrusion from moving toward the proximal end.

4. The medical device according to claim 1, wherein the lead angle of the stop portion is zero degrees, a positive angle, or a negative angle in a direction orthogonal to a central axis of the connector portion.

5. The medical device according to claim 1, wherein the inner cylinder has an internal screw groove configured to receive an external screw groove of the another medical device for fluid communication between the connector portion and the another medical device.

6. The medical device according to claim 1, wherein the engagement protrusion is a cylindrical protrusion.

7. The medical device according to claim 1, wherein the engagement protrusion comprises two or more protrusions.

8. The medical device according to claim 1, wherein the screw groove is a double thread groove and the engagement protrusion has two protrusions corresponding to the double thread groove.

9. The medical device according to claim 1, wherein an inclination in a cross section of an outer circumferential surface of the engagement protrusion is different from an inclination in a cross section of the stop portion along a central axis of the connector portion.

10. The medical device according to claim 1, wherein the valve body has an apical cylindrical head portion having a slit through which the spike is configured to penetrate, and a body portion which can be elastically deformed in a direction along a central axis of the connector portion.

11. A medical device comprising:
a connector portion having a distal end and a proximal end;
a screw groove configured for fluid communication between the connector portion and another medical device, wherein the screw groove has a first side wall on a distal side of the screw groove and a second side wall on a proximal side of the screw groove;
the connector portion having an outer cylinder and an inner cylinder, the inner cylinder arranged on a radially inner side of the outer cylinder, the outer cylinder including the screw groove and the inner cylinder having an engagement protrusion which is guided to the screw groove; and
a valve body arranged on a radially inner side of the inner cylinder and a spike capable of penetrating the valve body, and wherein the inner cylinder is biased toward the distal end by the valve body.

12. The medical device according to claim 11, further comprising:
a stop portion, the stop portion being on the first side wall, and wherein a lead angle of the first side wall changes slope relative to an adjacent first side wall portion; and
a stopper that abuts on the engagement protrusion, the engagement protrusion is configured to reach the stop portion, and wherein the stop portion is configured to prevent the engagement protrusion from moving toward the proximal end.

13. The medical device according to claim 11, wherein the inner cylinder has an internal screw groove configured to receive an external screw groove of the another medical device for fluid communication between the connector portion and the another medical device.

14. The medical device according to claim 11, wherein the valve body has an apical cylindrical head portion having a slit through which the spike is configured to penetrate, and a body portion which can be elastically deformed in a direction along a central axis of the connector portion.

* * * * *